United States Patent
Conroy et al.

(10) Patent No.: US 7,094,583 B2
(45) Date of Patent: Aug. 22, 2006

(54) NUCLEIC ACID DELIVERY

(75) Inventors: Susan E. Conroy, London (GB);
Engler Heidrun, San Diego, CA (US);
Daniel C. Maneval, San Diego, CA (US)

(73) Assignees: Canji, Inc., Kenilworth, NJ (US);
Innovata PLC, Ruddington (GB)

( * ) Notice: Subject to any disclaimer, the term of this patent is extended or adjusted under 35 U.S.C. 154(b) by 0 days.

(21) Appl. No.: 10/913,567

(22) Filed: Aug. 6, 2004

(65) Prior Publication Data
US 2005/0014259 A1  Jan. 20, 2005

Related U.S. Application Data

(63) Continuation of application No. 10/003,494, filed on Nov. 1, 2001, now abandoned.

(60) Provisional application No. 60/287,871, filed on Apr. 30, 2001, provisional application No. 60/245,539, filed on Nov. 3, 2000.

(51) Int. Cl.
*A61K 48/00* (2006.01)
*C12N 15/866* (2006.01)

(52) U.S. Cl. .................. 435/93.2; 435/320.1
(58) Field of Classification Search ............. 536/23.1; 514/44, 58; 435/320.1; 424/93.1, 93.2
See application file for complete search history.

(56) References Cited

U.S. PATENT DOCUMENTS 5,877,302 A * 3/1999 Hanson et al. ............ 536/23.1
6,066,468 A   5/2000 Burnham et al.
2003/0039960 A1 * 2/2003 Conroy et al. ............... 435/6
2003/0064949 A1 * 4/2003 Nielsen et al. ............. 514/44

FOREIGN PATENT DOCUMENTS

EP   0 935 967 A2   10/1998
GB      2027050 A *  1/1989
WO   WO 01/12231 A1  2/2001

OTHER PUBLICATIONS

Verma et al. Nature 389:239-242 (1997).*
Palu et al. J. Biotechnol. 68:1-13, 1999.*
Luo et al. Nature Biotechnology 18: 33-37, 2000.*
Fox, ASM News, Feb. 2000, 66(2): 1-3.*
Conroy, Susan et al. *In Vitro* Viral Vector Stability and Fluid Dynamics of an Intraperitoneal Solution for Delivery of Gene Therapy, Mar. 2002, Proceedings of the American Association for Cancer Research, vol. 41, p. 524.
Engler, Heidrun et al., Enhancement of intraperitoneal adenovirus mediated transgene expression by icodextrin in animal models, Nov. 2002, Clinical Cancer Research, vol. 6, No. 11, p. 516.
International Search Report and Notification of Transmittal of International Search Report (PCT/GB 01/04878) (8 sheets).

* cited by examiner

*Primary Examiner*—Nancy Vogel
(74) *Attorney, Agent, or Firm*—Townsend and Townsend and Crew, LLP

(57) ABSTRACT

The present invention provides formulations and methods to enhance the delivery of nucleic acids to cells. Formulations comprising dextrin polymers in combination with sugars provide enhanced delivery of nucleic acids, particularly eucaryotic expression vectors, demonstrate enhanced delivery of nucleic acids to cells in vivo. The present invention also provides methods of treatment in combination with such formulations.

26 Claims, 3 Drawing Sheets

NUCLEIC ACID DELIVERY

RELATION TO OTHER APPLICATIONS

The present application claims the benefit of U.S. Patent Provisional Application Ser. No. 60/245,539 filed Nov. 3, 2000 and U.S. Provisional Application Ser. No. 60/287,871 filed Apr. 30, 2001 pursuant to 35 U.S.C. § 119(e).

FIELD OF THE INVENTION

The invention relates to a method for the delivery of nucleic acid to cells, particularly but not exclusively, in gene therapy, including compositions the osmolarity of which corresponds substantially to the physiological osmolarity which surrounds the cell or tissue

BACKGROUND OF THE INVENTION

Many methods have been developed over the last 30 years to facilitate the introduction of nucleic acid into cells which have greatly assisted, inter alia, our understanding of the control of gene expression.

Conventional methods to introduce DNA into cells are well known in the art and typically involve the use of chemical reagents, cationic lipids or physical methods. Chemical methods which facilitate the uptake of DNA by cells include the use of DEAE-Dextran (Vaheri and Pagano, Science 175:434). DEAE-dextran associates with and introduces the DNA into cells. However this can result in loss of cell viability. Calcium phosphate is also a commonly used chemical agent which, when co-precipitated with DNA, introduces the DNA into cells (Graham et al Virology (1973) 52: 456).

The use of cationic lipids (e.g. liposomes (Felgner (1987) Proc.Natl.Acad.Sci USA, 84:7413) has become a common method since it does not have the degree of toxicity shown by the above described chemical methods. The cationic head of the lipid associates with the negatively charged nucleic acid backbone of the DNA to be introduced. The lipid/DNA complex associates with the cell membrane and fuses with the cell to introduce the associated DNA into the cell. Liposome mediated DNA transfer has several advantages over existing methods. For example, cells which are recalcitrant to traditional chemical methods are more easily transfected using liposome mediated transfer.

More recently still, physical methods to introduce DNA have become effective means to reproducibly transfect cells. Direct microinjection is one such method which can deliver DNA directly to the nucleus of a cell (Capecchi (1980) Cell, 22:p 479). This allows the analysis of single cell transfectants. So called "biolistic" methods physically insert DNA into cells and/or organelles using a high velocity particles coated with DNA (Neumann (1982) EMBO J, 1:841).

Electroporation is arguably the most popular method to transfect DNA. The method involves the use of a high voltage electrical charge to momentarily permeabilise cell membranes making them permeable to macromolecular complexes. However physical methods to introduce DNA do result in considerable loss of cell viability due to intracellular damage. These methods therefore require extensive optimisation and also require expensive equipment.

More recently still a method termed immunoporation has become a recognised techinque for the introduction of nucleic acid into cells, see Bildirici et al Nature (2000) 405, 298. The technique involves the use of beads coated with an antibody to a specific receptor. The transfection mixture includes nucleic acid, typically vector DNA, antibody coated beads and cells expressing a specific cell surface receptor. The coated beads bind the cell surface receptor and when a shear force is applied to the cells the beads are stripped from the cell surface. During bead removal a transient hole is created through which nucleic acid and/or other biological molecules can enter. Transfection efficiency of between 40–50% is achievable depending on the nucleic acid used.

Typically, gene therapy involves the transfer, and optionally the stable insertion, of new genetic information into cells for the therapeutic treatment of disease. Genes that have been successfully expressed in mice after transfer by retrovirus vectors include human hypoxanthine phosphoribosyl transferase (Miller A et al, 1984, Science 255:630). Bacterial genes have also been transferred into mammalian cells, in the form of bacterial drug resistance genes.

Transformation of hematopoietic progenitor cells to drug resistance by eukaryotic virus vectors has also accomplished with recombinant retrovirus based vector systems (Hock R A and Miller A D 1986, Nature 320:275–277; Joyner, et al. (1983) Nature 305:556–558; Williams D A et al 1984, Nature 310:476–480; Dick J E et al, 1985, Cell 42:71–79); Keller G et al 1985, Nature 318: 149–154; Eglitis M et al, 1985, Science 230: 1395–1398). Adeno-associated virus vectors have been used successfully to transduce mammalian cell lines to neomycin resistance (Hermonat P L and Muzyczka N, 1984, supra; Tratschin J D et al, 1985, Mol. Cell. Biol. 5:3251). Other viral vector systems that have been investigated for use in gene transfer include papovaviruses arid vaccinia viruses (See Cline, M L (1985) Pharmac. Ther. 29: 69–92).

The main issues with respect to gene therapy relate to the efficient targeting of nucleic acid to cells and the establishment of high level transgene expression in selected tissues. A number of methodologies have been developed which purport to facilitate either or both of these requirements. For example, U.S. Pat. No. 6,043,339 discloses the use of signal peptides which when fused to nucleic acid, can facilitate the translocation of the linked nucleic acid across cell membranes. U.S. Pat. No. 6,083,714 discloses a combined nucleic acid and targetting means which uses the polycation poly-lysine coupled to an integrin receptor thereby targetting cells expressing the integrin. EP1013770 discloses the use of nuclear localisation signals (NLS) coupled to oligonucleotides. The conjugate may be covalently linked to vector DNA and the complex used to transfect cells. The NLS sequence serves to facilitate the passage of the vector DNA across the nuclear membrane thereby targetting gene delivery to the nucleus.

Nucleic acid, for example vector DNA, may be introduced into an animal via a variety of routes including enterally (orally, rectally or sublingually) or parenterally (intravenously, subcutaneously, or by inhalation).

It is known that introduction of certain aqueous solutions into the peritoneal cavity can be useful in the treatment of patients suffering from renal failure. Such treatment is known as peritoneal dialysis. The solutions contain electrolytes similar to those present in plasma; they also contain an osmotic agent, normally dextrose, which is present in a concentration sufficient to create a desired degree of osmotic pressure across the peritoneal membrane. Under the influence of this osmotic pressure, an exchange takes place across the peritoneal membrane and results in withdrawal from the bloodstream of waste products, such as urea and creatinine, which have accumulated in the blood due to the lack of normal kidney function. While this exchange is taking place, there is also a net transfer of dextrose from the solution to the blood across the peritoneal membrane, which causes the osmolality of the solution to fall. Because of this, the initial osmolality of the solution must be made fairly high (by using a sufficiently high concentration of dextrose) in order that the solution continues to effect dialysis for a reasonable length of time before it has to be withdrawn and replaced by fresh solution.

Other osmotic agents have been proposed for use in peritoneal dialysis and in recent years dextrin (a starch hydrolysate polymer of glucose) has been used. When instilled in the peritoneal cavity, dextrin is slowly absorbed via the lymphatic system, eventually reaching the peripheral circulation. The structure of dextrin is such that amylases break the molecule down into oligosaccharides in the circulation. These are cleared by further metabolism into glucose.

Typically, a medium chosen to introduce gene therapy materials to a patient via a body cavity might be a buffered saline solution, for instance, phosphate buffered saline (PBS).

Dextrin solutions have been proposed as the medium for delivery of drugs to the body via the peritoneum. In GB-A-2207050, such a solution is proposed for the intraperitoneal administration of drugs for which enteral administration is unsatisfactory. Such an approach is stated to be particularly useful for the delivery of peptide drugs such as erythropoietin and growth hormones. Reference is also made to cephalosporin antibiotics. Dextrin solutions have also been described for the administration of chemotherapeutic agents in the treatment of ovarian cancers. The use of icodextrin formulations to increase the efficacy of chemotherapeutics (especially 5FU) by increasing their dwell time in the peritoneal space is well described in Dobbie J W. (1997) Adv Perit Dial. 13: 162–7 and McArdle C S, et al. (1994) Br J Cancer 70(4):762–6.

The present invention is directed to a dextrin containing solution which shows enhanced ability to deliver nucleic acid to cells resulting in high level expression of transfected genes.

SUMMARY OF THE INVENTION

The present invention provides a pharmaceutical formulation comprising a nucleic acid in a solution comprising dextrin and at least one sugar, the osmolarity of said solution corresponding substantially to physiological osmolarity.

The present invention further provides a method to deliver a nucleic acid to a cell wherein the nucleic acid is carried in a solution comprising dextrin and at least one sugar, the osmolarity of which corresponds substantially to the physiological osmolarity of the milieu surrounding the cell.

The invention further provides a method of treating an mammal with a nucleic acid wherein the nucleic acid is administered to said mammal in a pharmaceutical formulation comprising dextrin and at least one sugar.

DETAILED DESCRIPTION OF THE INVENTION

Figure 1:
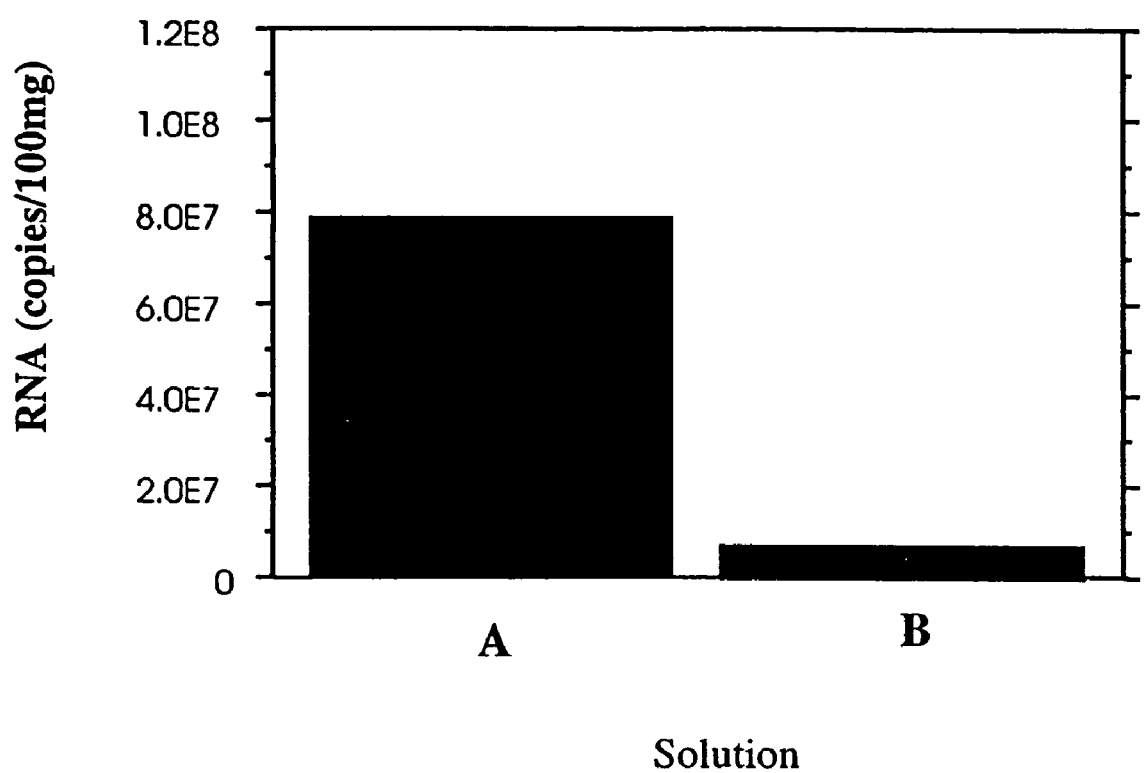
FIG. 1 is a histogram providing measuring the expression of the beta-galactosidase gene in epithelial tissues of the peritoneum in rabbits following the intraperitoneal instillation of a 100 ul of a solution containing a recombinant adenoviral vector encoding beta-galactosidase in various formulations as more fully described in Example 1 herein. The vertical axis represents the levels of viral RNA in tissues as determined by RT-PCR.

The present invention provides a pharmaceutical formulation comprising a nucleic acid in a solution comprising dextrin and at least one sugar, the osmolarity of said solution corresponding substantially to physiological osmolarity.

Dextrin:

The term "dextrin" means a glucose polymer which is produced by the hydrolysis of starch and which consists of glucose units linked together by means mainly of α-1,4 linkages. Typically dextrins are produced by the hydrolysis of starch obtained from various natural products such as wheat, rice, maize and tapioca. In addition to α-1,4 linkages there may be a proportion of α-1,6 linkages in a particular dextrin, the amount depending on the starch starting material. Since the rate of biodegradability of α-1,6 linkages is typically less than that for α-1,4 linkages, for many applications it is preferred that the percentage of α-1,6 linkages is less than 10% and preferably less than about 5%.

Any dextrin is a mixture of polyglucose molecules of different chain lengths. As a result, no single number can adequately characterise the molecular weight of such a polymer. Accordingly various averages are used, the most common being the weight average molecular weight (Mw) and the number average molecular weight (Mn). Mw is particularly sensitive to changes in the high molecular weights content of the polymer whilst Mn is largely influenced by changes in the low molecular weight of the polymer. It the preferred practice of the invention, the Mw of the dextrin is in the range from about 1,000 to 200,000, more preferably from about 2,000 to 55,000.

The term "degree of polymerisation" (DP) can also be used in connection with polymer mixtures. For a single polymer molecule, DP means the number of polymer units. For a mixture of molecules of different DP's, weight average DP and number average DP correspond to Mw and Mn. In addition DP can also be used to characterise a polymer by referring to the polymer mixture having a certain percentage of polymers of DP greater than a particular number or less than a particular number. It is preferred that, in the present invention, the dextrin contains more than about 15% of polymers of DP greater than 12 and, more preferably, more than about 50% of polymers of DP greater than 12.

Preferably the dextrin is present in the solution in an amount of less than about 20%. Preferably the dextrin is present in the solution in an amount selected from about: 1% (w/v); 2%(w/v); 3%(w/v); 4%(w/v); 5%(w/v); 6%(w/v); 7%(w/v); 8%(w/v); 9%(w/v); 10%(w/v); 11% w/v; 12% w/v; 13% w/v; 14% w/v; 15% w/v; 16% w/v; 17% w/v; 18% w/v; 19% w/v; 20% w/v. More preferably the dextrin is present from about 2 to 5% by weight, most preferably about 4% by weight.

Physiological Osmolarity:

As indicated, the solution possesses an osmolarity essentially isotonic with the osmolarity of the physiological milieu of the cell to be treated. Generally, the physiological osmolarity maintained in mammalian body cavities is approximately 330 milliosmolar and will vary somewhat with the particular body cavity. For example, an isotonic solution for instillation in the human peritoneal cavity would have an osmolarity of approximately 290–300 milliosmolar. In the preferred practice of the invention for intraperitoneal instillation, the solution will possess an osmolarity from about 250 to 350 milliosmolar, more preferably from about 275 to 330 milliosmolar. The adjustments to maintain approximate isotonic osmolarity depending on the particular physiological milieu will be readily apparent to those of skill in the art.

Sugar:

The term "sugar" refers to a monosaccharide, disaccharide or oligosaccharide. Monosaccharides have the empirical formula $(CH_2O)_n$ wherein n=3 or greater. Examples of monosaccharides, which are merely meant to be illustrative and not restrictive, are glucose, galactose, mannose, allose, altrose, gulose, idose, talose, fructose. Disaccharides consist of two monosaccharides linked by a glycoside bond. Non-restrictive examples of dissacharides are sucrose, maltose, cellobiose, gentiobiose, lactose. Typically oligosaccharides are sugars with more than two monosaccharide units. Non-restrictive examples of oligosaccharides are raffinose and melezitose. Sugars can be naturally occuring or industrially manufactured.

In a preferred method of the invention the sugar is a disaccharide. More preferably still the amount of disaccharide is between about 1–10% w/v. Preferably the amount of disaccharide is between about 2–5% w/v. In a preferred embodiment of the invention, the disaccharide is sucrose in is about 3% w/v.

In a further method of the invention the amount of dextrin is about between 2%–20% w/v and the amount of sucrose is about 1–10% w/v.

More ideally still the amount of dextrin is about 4% w/v and the amount of sucrose is about 3% w/v.

It will be apparent that the exact combination will depend on the osmolarity of the fluid surrounding the cell or tissue. Typically, it is desirable to maintain an isosmotic equilibrium between the solution including the nucleic acid and the fluid surrounding the cells/tissues.

Divalent Cation:

More preferably still said solution further comprises a divalent cation. Preferably the divalent cation is at least 0.2 mM. More preferably still the divalent cation concentration is between about 0.2–3.0 mM. Ideally the divalent cation is $MgCl_2$ and the concentration is about 2.0 mM. Alternatively the divalent cation is provided by $CaCl_2$.

Preferably the solution comprises about 4% w/v dextrin, about 3% w/v sucrose and about 2.0 mM $MgCl_2$. Alternatively, the dextrin concentration is about 15% w/v.

It will be apparent to one skilled in the art that the solution has utility with respect to the in vitro delivery of nucleic acid to cells for the recombinant production of polypeptides encoded by the nucleic acid. The invention also encompasses gene therapy, both the in vivo introduction of nucleic acid into cells and ex vivo introduction of nucleic acid into cells followed by introduction of transfected cells into an animal in need of gene therapy.

Nucleic Acid:

Preferably said nucleic acid molecule is adapted for eukaryotic expression. Typically said adaptation includes, by example and not by way of limitation, the provision of transcription control sequences (promoter sequences) which mediate cell/tissue specific expression. These promoter sequences may be cell/tissue specific, inducible or constitutive.

"Promoter" is an art recognised term and, for the sake of clarity, includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors (please see Eukaryotic Transcription Factors, by David S Latchman, Academic Press Ltd, San Diego) is responsive to a number of physiological/environmental cues which include, by example and not by way of limitation, intermediary metabolites (eg glucose, lipids), environmental effectors (eg light, heat,).

Promoter elements also include so called TATA box and RNA polymerase initiation selection (RIS) sequences which function to select a site of transcription initiation. These sequences also bind polypeptides which function, inter alia, to facilitate transcription initiation selection by RNA polymerase.

Adaptations also include the provision of selectable markers and autonomous replication sequences which facilitate the maintenance of said vector in either the eukaryotic cell or prokaryotic host. Vectors which are maintained autonomously are referred to as episomal vectors. Episomal vectors are desirable since these molecules can incorporate large DNA fragments (30–50 kb DNA). Episomal vectors of this type are described in WO98/07876.

Adaptations which facilitate the expression of vector encoded genes include the provision of transcription termination/polyadenylation sequences. This also includes the provision of internal ribosome entry sites (IRES) which function to maximise expression of vector encoded genes arranged in bi-cistronic or multi-cistronic expression cassettes. Expression control sequences also include so-called Locus Control Regions (LCRs). These are regulatory elements which confer position-independent, copy number-dependent expression to linked genes when assayed as transgenic constructs. LCRs include regulatory elements that insulate transgenes from the silencing effects of adjacent heterochromatin, Grosveld et al., Cell (1987), 51: 975–985.

Expression control sequences also encompass, ubiquitous chromatin opening elements (UCOE's), see WO/GB00/05393. UCOE's are nucleic acid elements that are responsible for establishing an open chromatin structure across a locus that consists exclusively of ubiquitously expressed, housekeeping genes. These elements are not derived from an LCR. A UCOE is a polynucleotide which opens chromatin or maintains chromatin in an open state and facilitates-reproducible expression of an operably-linked gene in cells of at least two different tissue types.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

Vectors are typically viral based and may be derived from viruses including adenovirus; retrovirus; adeno-associated virus; herpesvirus; lentivirus; vaccinia virus; and baculovirus.

The terms "therapeutic virus" and "therapeutic viral vector" are used interchangeably herein to refer to viruses used as therapeutic agents (e.g. wild-type viruses, attenuated viruses), vaccine vectors or recombinant viruses containing modifications to the genome to enhance therapeutic effects. The use of viruses or "viral vectors" as therapeutic agents are well known in the art as previously discussed. Additionally, a number of viruses are commonly used as vectors for the delivery of exogenous genes. Commonly employed vectors include recombinantly modified enveloped or non-enveloped DNA and RNA viruses, preferably selected from baculoviridiae, parvoviridiae, picomoviridiae, herpesveridiae, poxviridae, adenoviridiae, or picornnaviridiae. Chimeric vectors may also be employed which exploit advantageous elements of each of the parent vector properties (See e.g., Feng, et al.(1997) Nature Biotechnology 15: 866–870). Such viral vectors may be wild-type or may be modified by recombinant DNA techniques to be replication deficient, conditionally replicating or replication competent.

Preferred vectors are derived from the adenoviral, adeno-associated viral and retroviral genomes. In the most preferred practice of the invention, the vectors are derived from the human adenovirus genome. Particularly preferred vectors are derived from the human adenovirus serotypes 2 or 5. The replicative capacity of such vectors may be attenuated (to the point of being considered "replication deficient") by modifications or deletions in the E1a and/or E1b coding regions. Other modifications to the viral genome to achieve particular expression characteristics or permit repeat administration or lower immune response are preferred. Most preferred are human adenoviral type 5 vectors containing a DNA sequence encoding the p53 tumor suppressor gene. In the most preferred practice of the invention as exemplified herein, the vector is replication deficient vector adenoviral vector encoding the p53 tumor suppressor gene A/C/N/53 as described in Gregory, et al., U.S. Pat. No. 5,932,210 issued Aug. 3, 1999 (the entire teaching of which is herein incorporated by reference).

Alternatively, the viral vectors may be conditionally replicating or replication competent. Conditionally replicating viral vectors are used to achieve selective expression in particular cell types while avoiding untoward broad spectrum infection. Examples of conditionally replicating vectors are described in Pennisi, E. (1996) Science 274:342–343; Russell, and S. J. (1994) Eur. J. of Cancer 30A(8):1165–1171. Additional examples of selectively replicating vectors include those vectors wherein an gene essential for replication of the virus is under control of a promoter which is active only in a particular cell type or cell state such that in the absence of expression of such gene, the virus will not replicate. Examples of such vectors are described in Henderson, et al., U.S. Pat. No. 5,698,443 issued Dec. 16, 1997 and Henderson, et al., U.S. Pat. No. 5,871,726 issued Feb. 16, 1999 the entire teachings of which are herein incorporated by reference.

Additionally, the viral genome may be modified to include inducible promoters which achieve replication or expression only under certain conditions. Examples of inducible promoters are known in the scientific literature (See, e.g. Yoshida and Hamada (1997) Biochem. Biophys. Res. Comm. 230:426–430; Iida, et al. (1996) J. Virol. 70(9): 6054–6059; Hwang, et al.(1997) J. Virol 71(9):7128–7131; Lee, et al. (1997) Mol. Cell. Biol. 17(9):5097–5105; and Dreher, et al.(997) J. Biol. Chem 272(46); 29364–29371.

The viruses may also be designed to be selectively replicating viruses. Particularly preferred selectively replicating viruses are described in Ramachandra, et al. PCT International Publication No. WO 00/22137, International Application No. PCT/US99/21452 published Apr. 20, 2000 and Howe, J., PCT International Publication No. WO WO0022136, International Application No. PCT/US99/21451 published Apr. 20, 2000. A particularly preferred selectively replicating recombinant adenovirus is the virus dl01/07/309 as more fully described in Howe, J.

It has been demonstrated that viruses which are attenuated for replication are also useful in the therapeutic arena. For example the adenovirus dl1520 containing a specific deletion in the E1b55K gene (Barker and Berk (1987) Virology 156: 107) has been used with therapeutic effect in human beings. Such vectors are also described in McCormick (U.S. Pat. No. 5,677,178 issued Oct. 14, 1997) and McCormick, U.S. Pat. No 5,846,945 issued Dec. 8, 1998. The method of the present invention may also be used in combination with the administration of such vectors to minimize the pre-existing or induced humoral immune response to such vectors.

Additionally, the therapeutic virus may incorporate a therapeutic transgene for expression in an infected cell. The term "therapeutic transgene" refers to a nucleotide sequence the expression of which in the target cell produces a therapeutic effect. The term therapeutic transgene includes but is not limited to tumor suppressor genes, antigenic genes, cytotoxic genes, cytostatic genes, pro-drug activating genes, apoptotic genes, pharmaceutical genes or anti-angiogenic genes. The vectors of the present invention may be used to produce one or more therapeutic transgenes, either in tandem through the use of IRES elements or through independently regulated promoters.

The term "tumor suppressor gene" refers to a nucleotide sequence, the expression of which in the target cell is capable of suppressing the neoplastic phenotype and/or inducing apoptosis. Examples of tumor suppressor genes useful in the practice of the present invention include the p53 gene, the APC gene, the DPC-4 gene, the BRCA-1 gene, the BRCA-2 gene, the WT-1 gene, the retinoblastoma gene (Lee, et al. (1987) Nature 329:642), the MMAC-1 gene, the adenomatous polyposis coli protein (Albertsen, et al., U.S. Pat. No. 5,783,666 issued Jul. 21, 1998), the deleted in colon carcinoma (DCC) gene, the MMSC-2 gene,. the NF-1 gene, nasopharyngeal carcinoma tumor suppressor gene that maps at chromosome 3p21.3. (Cheng, et al. 1998. Proc. Nat. Acad. Sci. 95:3042–3047), the MTIS1 gene, the CDK4 gene, the NF-1 gene, the NF2 gene, and the VHL gene. A particularly preferred adenovirus for therapeutic use is the A/C/N/53 vector encoding the p53 tumor suppressor gene as more fully described in Gregory, et al., U.S. Pat. No. 5,932,210 issued Aug. 3, 1999, the entire teaching of which is herein incorporated by reference.

The term "antigenic genes" refers to a nucleotide sequence, the expression of which in the target cells results in the production of a cell surface antigenic protein capable of recognition by the immune system. Examples of antigenic genes include carcinoembryonic antigen (CEA), p53 (as described in Levine, A. PCT International Publication No. WO94/02167 published Feb. 3, 1994). In order to facilitate immune recognition, the antigenic gene may be fused to the MHC class I antigen. Preferably the antigenic gene is derived from a tumour cell specific antigen. Ideally a tumour rejection antigen. Tumour rejection antigens are well known in the art and include, by example and not by way of limitation, the MAGE, BAGE, GAGE and DAGE families of tumour rejection antigens, see Schulz et al Proc Natl Acad Sci USA, 1991, 88, pp 991–993.

It has been known for many years that tumour cells produce a number of tumour cell specific antigens, some of which are presented at the tumour cell surface. These are generally referred to as tumour rejection antigens and are derived from larger polypeptides referred to as tumour rejection antigen precursors. Tumour rejection antigens are presented via HLA's to the immune system. The immune system recognises these molecules as foreign and naturally selects and destroys cells expressing these antigens. If a transformed cell escapes detection and becomes established a tumour develops. Vaccines have been developed based on dominant tumour rejection antigen's to provide individuals with a preformed defence to the establishment of a tumour.

The term "cytotoxic gene" refers to nucleotide sequence, the expression of which in a cell produces a toxic effect. Examples of such cytotoxic genes include nucleotide sequences encoding pseudomonas exotoxin, ricin toxin, diptheria toxin, and the like.

The term "cytostatic gene" refers to nucleotide sequence, the expression of which in a cell produces an arrest in the cell cycle. Examples of such cytostatic genes include p21, the retinoblastoma gene, the E2F—Rb gene, genes encoding cyclin dependent kinase inhibitors such as P16, p15, p18 and p19, the growth arrest specific homeobox (GAX) gene as described in Branellec, et al. (PCT Publication WO97/16459 published May 9, 1997 and PCT Publication WO96/30385 published Oct. 3, 1996).

The term "cytokine gene" refers to a nucleotide sequence, the expression of which in a cell produces a cytokine. Examples of such cytokines include GM-CSF, the interleukins, especially IL1, IL-2, IL-4, IL-12, IL-10, IL-19, IL-20, interferons of the α, β and γ subtypes, consensus interferons and especially interferon α-2b and fusions such as interferon α-2α-1.

The term "chemokine gene" refers to a nucleotide sequence, the expression of which in a cell produces a cytokine. The term chemokine refers to a group of structurally related low-molecular cytokines weight factors secreted by cells are structurally related having mitogenic, chemotactic or inflammatory activities. They are primarily cationic proteins of 70 to 100 amino acid residues that share four conserved cysteine. These proteins can be sorted into two groups based on the spacing of the two amino-terminal cysteines. In the first group, the two cysteines are separated by a single residue (C-x-C), while in the second group, they are adjacent (C-C). Examples of member of the 'C-x-C' chemokines include but are not limited to platelet factor 4 (PF4), platelet basic protein (PBP), interleukin-8 (IL-8), melanoma growth stimulatory activity protein (MGSA), macrophage inflammatory protein 2 (MIP-2), mouse Mig (m119), chicken 9E3 (or pCEF-4), pig alveolar macrophage chemotactic factors I and II (AMCF-I and -II), pre-B cell growth stimulating factor (PBSF),and IP10. Examples of members of the 'C—C' group include but are not limited to monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1 α (MP-1-α), macrophage inflammatory protein 1 β (MIP-1-β), macrophage inflammatory protein 1-γ (MIP-1-γ), macrophage inflammatory protein 3 α (MIP-3-α, macrophage inflammatory protein 3 β (MIP-3-β), chemokine (ELC), macrophage inflammatory protein-4 (MIP-4), macrophage inflammatory protein 5 (MIP-5), LD78 β, RANTES, SIS-epsilon (p500), thymus and activation-regulated chemokine (TARC), eotaxin, I-309, human protein HCC-1/NCC-2, human protein HCC-3, mouse protein C10.

The term "pharmaceutical protein gene" refers to nucleotide sequence, the expression of which results in the production of protein have pharmaceutically effect in the target cell. Examples of such pharmaceutical genes include the proinsulin gene and analogs (as described in PCT International Patent Application No. WO98/31397, growth hormone gene, dopamine, serotonin, epidermal growth factor, GABA, ACTH, NGF, VEGF (to increase blood perfusion to target tissue, induce angiogenesis, PCT publication WO98/32859 published Jul. 30, 1998), thrombospondin etc. Also, the pharmaceutical protein gene may encompass immunoreactive proteins such as antibodies, Fab fragments, Fv fragments, humanized antibodies, chimeric antibodies, single chain antibodies, and human antibodies derived from non-human sources.

The term "pro-apoptotic gene" refers to a nucleotide sequence, the expression thereof results in the induction of the programmed cell death pathway of the cell. Examples of pro-apoptotic genes include p53, adenovirus E3-11.6K (10.5K), the adenovirus E4orf4 gene, p53 pathway genes, and genes encoding the caspases.

The term "pro-drug activating genes" refers to nucleotide sequences, the expression of which, results in the production of protein capable of converting a non-therapeutic compound into a therapeutic compound, which renders the cell susceptible to killing by external factors or causes a toxic condition in the cell. An example of a prodrug activating gene is the cytosine deaminase gene. Cytosine deaminase converts 5-fluorocytosine to 5 fluorouracil, a potent antitumor agent). The lysis of the tumor cell provides a localized burst of cytosine deaminase capable of converting 5FC to 5FU at the localized point of the tumor resulting in the killing of many surrounding tumor cells. This results in the killing of a large number of tumor cells without the necessity of infecting these cells with an adenovirus (the so-called bystander effect"). Additionally, the thymidine kinase (TK) gene (see e.g. Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir may be employed.

The term "anti-angiogenic" genes refers to a nucleotide sequence, the expression of which results in the extracellular secretion of anti-angiogenic factors. Anti-angiogenesis factors include angiostatin, inhibitors of vascular endothelial growth factor (VEGF) such as Tie 2 (as described in PNAS(USA)(1998) 95:8795–8800), endostatin.

It will be readily apparent to those of skill in the art that modifications and or deletions to the above referenced genes so as to encode functional subfragments of the wild type protein may be readily adapted for use in the practice of the present invention. For example, the reference to the p53 gene includes not only the wild type protein but also modified p53 proteins. Examples of such modified p53 proteins include modifications to p53 to increase nuclear retention, deletions such as the Δ13–19 amino acids to eliminate the calpain consensus cleavage site (Kubbutat and Vousden (1997) Mol. Cell. Biol. 17:460–468, modifications to the oligomerization domains (as described in Bracco, et al. PCT published application WO97/0492 or U.S. Pat. No. 5,573,925, etc.).

It will be readily apparent to those of skill in the art that the above therapeutic genes may be secreted into the media or localized to particular intracellular locations by inclusion of a targeting moiety such as a signal peptide or nuclear localization signal (NLS). Also included in the definition of therapeutic transgene are fusion proteins of the therapeutic transgene with the herpes simplex virus type 1 (HSV-1) structural protein, VP22. Fusion proteins containing the VP22 signal, when synthesized in an infected cell, are exported out of the infected cell and efficiently enter surrounding non-infected cells to a diameter of approximately 16 cells wide. This system is particularly useful in conjunction with transcriptionally active proteins (e.g. p53) as the fusion proteins are efficiently transported to the nuclei of the surrounding cells. See, e.g.Elliott, G. & O'Hare, P. Cell. 88:223–233:1997; Marshall, A. & Castellino, A. Research News Briefs. Nature Biotechnology. 15:205:1997; O'Hare, et al. PCT publication WO97/05265 published Feb. 13, 1997. A similar targeting moiety derived from the HIV Tat protein is also described in Vives, et al. (1997) J. Biol. Chem. 272:16010–16017.

It may be valuable in some instances to utilize or design vectors to achieve introduction of the exogenous transgene in a particular cell type. Certain vectors exhibit a natural tropism for certain tissue types. For example, vectors derived from the genus herpesviridae have been shown to have preferential infection of neuronal cells. Examples of recombinantly modified herpesviridae vectors are disclosed in U.S. Pat. No. 5,328,688 issued Jul. 12, 1994. Cell type specificity or cell type targeting may also be achieved in vectors derived from viruses having characteristically broad infectivities by the modification of the viral envelope proteins. For example, cell targeting has been achieved with adenovirus vectors by selective modification of the viral genome knob and fiber coding sequences to achieve expression of modified knob and fiber domains having specific interaction with unique cell surface receptors. Examples of such modifications are described in Wickham, et al.(1997) J. Virol 71(11):8221–8229 (incorporation of RGD peptides into adenoviral fiber proteins); Arnberg, et al.(1997) Virology 227:239–244 (modification of adenoviral fiber genes to achieve tropism to the eye and genital tract); Harris and Lemoine (1996) TIG 12(10):400–405; Stevenson, et al. (1997) J. Virol. 71(6):4782–4790; Michael, et al.(1995) Gene Therapy 2:660–668 (incorporation of gastrin releasing peptide fragment into adenovirus fiber protein); and Ohno, et al.(1997) Nature Biotechnology 15:763–767 (incorporation of Protein A-IgG binding domain into Sindbis virus). Other methods of cell specific targeting have been achieved by the conjugation of antibodies or antibody fragments to the envelope proteins (see, e.g. Michael, et al. (1993) J. Biol. Chem 268:6866–6869, Watkins, et al. (1997) Gene Therapy 4:1004–1012; Douglas, et al.(1996) Nature Biotechnology 14:1574–1578. Alternatively, particularly moieties may be conjugated to the viral surface to achieve targeting (See, e.g. Nilson, et al. (1996) Gene Therapy 3:280–286 (conjugation of EGF to retroviral proteins)). Additionally, the virally encoded therapeutic transgene also be under control of a tissue specific promoter region allowing expression of the transgene preferentially in particular cell types.

Vectors may also be non-viral and are available from a number of commercial sources readily available to the man-skilled in the art. For example the vectors may be plasmids which can be episomal or integrating plasmids.

In a further preferred embodiment of the invention said nucleic acid is an antisense nucleic acid, preferably an antisense oligonucleotide.

As used herein, the term "antisense oligonucleotide" or "antisense" describes an that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and thereby, inhibits the transcription of that gene and/or the translation of that mRNA. Antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence.

It is preferred that the antisense oligonucleotide be constructed and arranged so as to bind selectively with the target under physiological conditions, i.e., to hybridize substantially more to the target sequence than to any other sequence in the target cell under physiological conditions.

In order to be sufficiently selective and potent for inhibition, such antisense oligonucleotides should comprise at least 7 (Wagner et al., Nature Biotechnology 14:840–844, 1996) and more preferably, at least 15 consecutive bases which are complementary to the target. Most preferably, the antisense oligonucleotides comprise a complementary sequence of 20–30 bases.

Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. The 3'-untranslated regions are known to contain cis acting sequences which act as binding sites for proteins involved in stabilising mRNA molecules. These cis acting sites often form hairloop structures which function to bind said stabilising proteins. A well known example of this form of stability regulation is shown by histone mRNA's, the abundance of which is controlled, at least partially, post-transcriptionally.

The term "antisense oligonucleotides" is to be construed as materials manufactured either in vitro using conventional oligonucleotide synthesising methods which are well known in the art or oligonucleotides synthesised recombinantly using expression vector constructs. Modified oligonucleotide is construed in the following manner. The term "modified oligonucleotide" as used herein describes an oligonucleotide in which;

i) at least two of its nucleotides are covalently linked via a synthetic internucleoside linkage (i.e., a linkage other than a phosphodiester linkage between the 5' end of one nucleotide and the 3' end of another nucleotide). Alternatively or preferrably said linkage may be the 5' end of one nucleotide linked to the 5' end of another nucleotide or the 3' end of one nucleotide with the 3' end of another nucleotide; and/or ii) a chemical group not normally associated with nucleic acids has been covalently attached to the oligonucleotide or oligoribonucleotide. Preferred synthetic internucleoside linkages are phosphorothioates, alkylphosphonates, phosphorodithioates, phosphate esters, alkylphosphonothioates, phosphoramidates, carbamates, phosphate triesters, acetamidates, peptides, and carboxymethyl esters.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. Modified oligonucleotides also can include base analogs such as C-5 propyne modified bases (Wagner et al., Nature Biotechnology 14:840–844, 1996).

The present invention, thus, contemplates pharmaceutical preparations containing natural and/or modified antisense molecules that are complementary to and, under physiological conditions, hybridizable with nucleic acids encoding proteins the regulation of which results in beneficial therapeutic effects, together with pharmaceutically acceptable carriers (eg polymers, liposomes/cationic lipids).

Antisense oligonucleotides may be administered as part of a pharmaceutical composition. Such a pharmaceutical composition may include the antisense oligonucleotides in combination with any standard physiologically and/or pharmaceutically acceptable carriers which are known in the art (eg liposomes). The compositions should be sterile and contain a therapeutically effective amount of the antisense oligonucleotides for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism.

In yet a still further preferred method of the invention said nucleic acid is a double stranded RNA molecule (RNA). A technique to specifically ablate gene function is through the introduction of double stranded RNA, also referred to as inhibitory RNA (RNAi), into a cell which results in the destruction of mRNA complementary to the sequence included in the RNAi molecule. The RNAi molecule comprises two complementary strands of RNA (a sense strand and an antisense strand) annealed to each other to form a double stranded RNA molecule. The RNAi molecule is typically derived from exonic or coding sequence of the gene which is to be ablated. In a preferred method of the invention the length of the RNAi molecule is between 100 bp–1000 bp. More preferably still the length of RNAi is selected from about 100 bp; 200 bp; 300 bp; 400 bp; 500 bp; 600 bp; 700 bp; 800 bp; 900 bp; or 1000 bp. More preferably still said RNAi is at least 1000 bp.

In a further preferred method of the invention said RNAi is derived from an exon.

Alternatively said RNAi molecule is derived from intronic sequences or the 5' and/or 3' non-coding sequences which flank coding/exon sequences of genes. Recent studies suggest that RNAi molecules ranging from 100–1000 bp derived from coding sequence are effective inhibitors of gene expression. Suprisingly, only a few molecules of RNAi are required to block gene expression which implies the mechanism is catalytic. The site of action appears to be nuclear as little if any RNAi is detectable in the cytoplasm of cells indicating that RNAi exerts its effect during MRNA synthesis or processing.

In yet a further preferred method of the invention said RNAi molecules comprise modified ribonucleotide bases. It will be apparent to one skilled in the art that the inclusion of modified bases, as well as the naturally occuring bases cytosine, uracil, adenosine and guanosine, may confer advantageous properties on RNAi molecules containing said modified bases. For example, modified bases may increase the stability of the RNAi molecule thereby reducing the amount required to produce a desired effect.

The exact mechanism of RNAi action is unknown although there are theories to explain this phenomenon. For example, all organisms have evolved protective mechanisms to limit the effects of exogenous gene expression. For example, a virus often causes deleterious effects on the organism it infects. Viral gene expression and/or replication therefore needs to be repressed. In addition, the rapid development of genetic transformation and the provision of transgenic plants and animals has led to the realisation that transgenes are also recognised as foreign nucleic acid and subjected to phenomena variously called quelling (Singer and Selker, Curr Top Microbiol Immunol. 1995;197:165–77), gene silencing (Matzkeand Matzke, Novartis Found Symp. 1998;214:168–80; discussion 181–6. Review) and co-suppression (Stam et. al., Plant J. 2000;21 (1):27–42.

Initial studies using RNAi used the nematode *Caenorhabditis elegans*. RNAi injected into the worm resulted in the disappearance of polypeptides corresponding to the gene sequences comprising the RNAi molecule(Montgomery et. al., 1998; Fire et. al., 1998). More recently the phenomenon of RNAi inhibition has been shown in a number of eukaryotes including, by example and not by way of limitation, plants, trypanosomes (Shi et. al., 2000) *Drosophila* spp. (Kennerdell and Carthew, 2000). Recent experiments have shown that RNAi may also function in higher eukaryotes. For example, it has been shown that RNAi can ablate c-mos in a mouse ooctye and also E-cadherin in a mouse preimplanation embryo (Wianny and Zernicka-Goetz, 2000).

In a yet further preferred method of the invention said nucleic acid is a ribozyme. A ribozyme is a catalytic RNA which is well known in the art. A ribozyme comprises a catalytic core having flanking sequences adjacent to the sequence which hybridises to the substrate RNA. The simplest catalytic core is an RNA motif known as a hammerhead. Since the discovery of catalytic RNA there has been a desire to design ribozymes which have a targetted gene function such that viral MRNA and disease gene mRNA's can be selectively ablated. For example, U.S. Pat. No. 6,069,007 discloses ribozymes active against HIV1 mRNA and their use in AIDS therapy. U.S. Pat. No. 6,087,172 discloses ribozymes designed to ablate mRNA encoding IL-15, an interleukin invloved in rheumatoid arthritis. U.S. Pat. No. 6,077,705 discloses a method of gene therapy to inhibit the expression of mutated genes combined with the replacement of the mutated gene, in this example α-1-antitrypsin, with a wild-type copy.

Modes of Administration/Treatment:

The formulations of the present invention are useful for enhancing the transfer of nucleic acids into tissues. It will be apparent to one skilled in the art that solutions according to the invention may be introduced into an animal subject in a variety of ways including enterally (orally, rectally or sublingually) or parenterally (intravenously, subcutaneously, or by inhalation). The solutions may be provided to the mammal by implanted catheters, In the preferred practice of the invention, the solutions are instilled into a body cavity to facilitate transduction of the surrounding tissues. Examples of such body cavities into which the solutions may be provided for the delivery of nucleic acids include the peritoneal cavity, pleural cavity, and the abdominal cavity. Additionally the solutions may be provided in other fluid containing spaces such as cerebral spinal fluid, joints, the colon, the bladder, the eye and gall bladder. It will also be apparent to one skilled in the art that the solutions can be administered simultaneously, (as an admixture), separately or sequentially to an animal.

According to a further aspect of the invention there is provided a composition comprising dextrin, a sugar, divalent cation and a nucleic acid molecule. Preferably said composition is for use in the delivery of nucleic acid for gene therapy. In the preferred practice of the invention, this procedure is employed in conjunction with recombinant adenoviral therapy for the treatment of human cancers. In accordance with conventional oncology practice, patients are dosed at the maximum tolerated dose of the therapeutic agent. In the course of clinical investigation, a dose of $7.5 \times 10^{13}$ recombinant adenoviral particles was well tolerated in human subjects. Clinical experience with replication deficient recombinant adenoviruses expressing p53 has indicated that a course of therapy of injection of approximately $7.5 \times 10^{13}$ recombinant viral particles for a period of 5 day course of therapy repeated monthly up to five months is effective in the treatment of ovarian cancer in human beings.

In a particularly preferred embodiment of the present invention, a formulation of the present invention comprising a replication deficient recombinant adenovirus encoding p53 is instilled into the peritoneum for the treatment of ovarian cancer. A typical course of therapy with this agent involves administration of $7.5 \times 10^{13}$ viral particles each day for a period of 5 days. A typical clinical protocol for the treatment of ovarian cancer using the A/C/N/53 virus calls involves a typical 5 day course of therapy described above in conjunction with the administration of the chemotherapeutic agents carboplatin and paclitaxel. In the preferred practice of the invention the mammal is a human being which receives three or more courses of therapy, preferably 5–6 courses of therapy, with intervening rest periods. Modifications to this procedure for therapeutic viruses other than adenovirus will be readily apparent to the skilled artisan The formulations of the present invention may further comprise additional carriers, excipients or diluants. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

EXAMPLES

The following examples are merely illustrative of the practice of the present invention and are not intended to limit the scope thereof.

Example 1

Enhancement of rAd-Mediated Transgene Expression in Rabbits (Intraperitoneal Administration) Using an Icodextrin Formulation In order to evaluate the ability to enhance transgene expression from a recombinant adenoviral vectors, an experiment was conducted to compare the relative levels of transgene expression. A recombinant adenoviral vector encoding the beta-galactosidase gene (rAd-bgal) was prepared in substantial accordance with the teach of Gregory, et al., U.S. Pat. No. 5,932,210. The following solutions were preparedin a volume of 100 ml.

| Solution | Components |
|---|---|
| A | $1 \times 10^9$ particles/ml of rAd-bgal in 15% w/v icodextrin containing 3% sucrose, 2 mM magnesium, 95 mM sodium, 1.75 mM calcium, 59 mM chloride, 40 mM lactate |
| B | $1 \times 10^9$ particles/ml of rAd-bgal, 3% sucrose, 2 mM magnesium chloride in phosphate buffered saline |

Ten female New Zealand white rabbits were anaesthetized with ketamine/xylazine and the foregoing solutions instilled intraperitoneally. The solution was allowed to incubate for 1 hour (at dorsal side) and one hour (at ventral side). The animals were sacrificed and biopsies of the peritoneal wall were harvested. Levels of viral RNA in harvested tissues was assayed using RT-PCR. The results of transgene specific RNA concentrations isolated from the peritoneal wall are presented in FIG. 1 of the accompanying drawings. As can be seen from the data presented addition of 15% icodextrin to the virus buffer solution (solution A) resulted in a marked increase in transgene expression relative to the buffer control solution alone (solution B).

Example 2

Efficacy of Icodextrin rAd-p53 Formulation in Murine Xenograft Prostate Cancer Model In order to demonstrate that the icodextrin containing formulations of recombinant adenoviruses provide an enhanced therapeutic effect, a experiment was conducted to compare the anti-tumor efficacy of replication deficient recombinant adenoviral vectors encoding the p53 tumor suppressor gene ("rAd-p53"). The efficacy of the vectors was compared in a murine xenograft prostate cancer model as described in Paine-Murrieta G D et al. Cancer Chemother Pharmacol 1997, 40: 209. Increased survival was used as the measure of efficacy.

The rAd-p53 vector designated ACN53 was prepared in substantial accordance with the teaching of Gregory, et al., U.S. Pat. No. 5,932,210. PC-3 prostate cancer cells were obtained from the American Type Culture Collection, Bethesda Md. under accession number CRL-1435. Fifty-one female nude mice, approximately 5 weeks old were obtained from Harlan Laboratories. Approximately $5 \times 10^6$ PC3 cells in a volume of 0.2 ml of HBSS-FBS (Hanks Balanced Salt Solution w/10% fetal bovine serum; HBSS was obtained from Fisher Scientific, FBS was obtained from BioWhittaker) were injected intraperitoneally into each animal. The cells were allowed to establish tumors for a period of nine days prior to the initiation of treatment.

Seven different formulations were prepared in accordance with Table 2 below:

TABLE 2

Formulations

| Name | Description | vPBS (1) (microliters) | vICO (2) (milliliters) | virus (3) (microliters) |
|---|---|---|---|---|
| A | 15% vICO control | 0 | 5 | 0 |
| B | $1 \times 10^{10}$ PN ACN53; 15% vICO | 549 | 7.2 | 251 |
| C | $1 \times 10^{10}$ PN ACN53; vPBS | 7749 | 0 | 251 |
| D | $1 \times 10^{9}$ PN ACN53; 15% vICO | 775 | 7.2 | 25.1 |
| E | $1 \times 10^{9}$ PN ACN53; vPBS | 7975 | 0 | 25.1 |
| F | $1 \times 10^{8}$ PN ACN53; 15% vICO | 775 | 7.2 | 2.51* |
| G | $1 \times 10^{8}$ PN ACN53; vPBS | 7975 | 0 | 2.51* |

Notes:
(1) "vPBS" solution is a sterile solution 3% sucrose, 2 mM $MgCl_2$ in phosphate buffered saline, pH7.4.
(2) "vICO" is a sterile 15% icodextrin solution 95 millimolar $Na^+$, 1.75 millimolar $Ca^{++}$, 2.0 millimolar $Mg^{++}$, 59 millimolar $Cl^-$, 40 millimolar lactate, 88 millimolar sucrose, 160 g/liter icodextrin, having a final osmolarity of 285.75.
(3) "virus" refers to a stock virus suspension containing $3.19 \times 10^{11}$ ACN53 viral particles per milliliter. As it is difficult to measure 2.51 microliters with conventional equipment, formulations F and G were prepared by the addition of 25.1 microliters of a 1:10 dilution of the stock viral suspension in vPBS to achieve the equivalent of 2.51 microliters of virus suspension.

The animals were divided up into eight treatment groups as more fully described in Table 3 below:

TABLE 3

Treatment Groups

| Group | n | Formulation | Total ACN53 Dose (particles) |
|---|---|---|---|
| 1 | 5 | untreated | — |
| 2 | 4 | A | — |
| 3 | 7 | B | $5 \times 10^{10}$ |
| 4 | 7 | C | $5 \times 10^{10}$ |
| 5 | 7 | D | $5 \times 10^{9}$ |
| 6 | 7 | E | $5 \times 10^{9}$ |
| 7 | 7 | F | $5 \times 10^{8}$ |
| 8 | 7 | G | $5 \times 10^{8}$ |

Treatment was initiated on Day 9. (Note: All treatment days denoted by "Day" mentioned herein are referenced from the date of injection of the PC-3 cells) All animals appeared healthy upon initiation of the treatment regimen. Other than the untreated control group 1, each group was provided a treatment regimen consisting of treatments each consisting of a single intraperitoneal injection of 1.0 ml of the appropriate formulation on Days 9, 11, 14, 15 and 18 following injection of tumor cells. Upon completion of the treatment regimen, the animals were randomly caged and monitored daily (blinded) for sick animals as charactized by visible loss of body weight hunched back, and sedation. Sick animals were sacrificed and examined gross pathologically. Animal number, date of sacrifice (or found dead) and gross pathological findings were recorded. The results are summarized in Table 4 below:

TABLE 4

Results of PC-3 Tumor Model

| | | Survival Time (Days) | | |
|---|---|---|---|---|
| Group | Formulation | median | minimum | maximum |
| 1 | untreated | 30 | 23 | 33 |
| 2 | A | 30 | 21 | 33 |
| 3 | B | 53 | 30 | 100* |
| 4 | C | 33 | 21 | 42 |
| 5 | D | 36 | 21 | 55 |
| 6 | E | 21 | 21 | 36 |
| 7 | F | 36 | 21 | 42 |
| 8 | G | 36 | 21 | 39 |

*the experiment was concluded on Day 100

Figure 2:
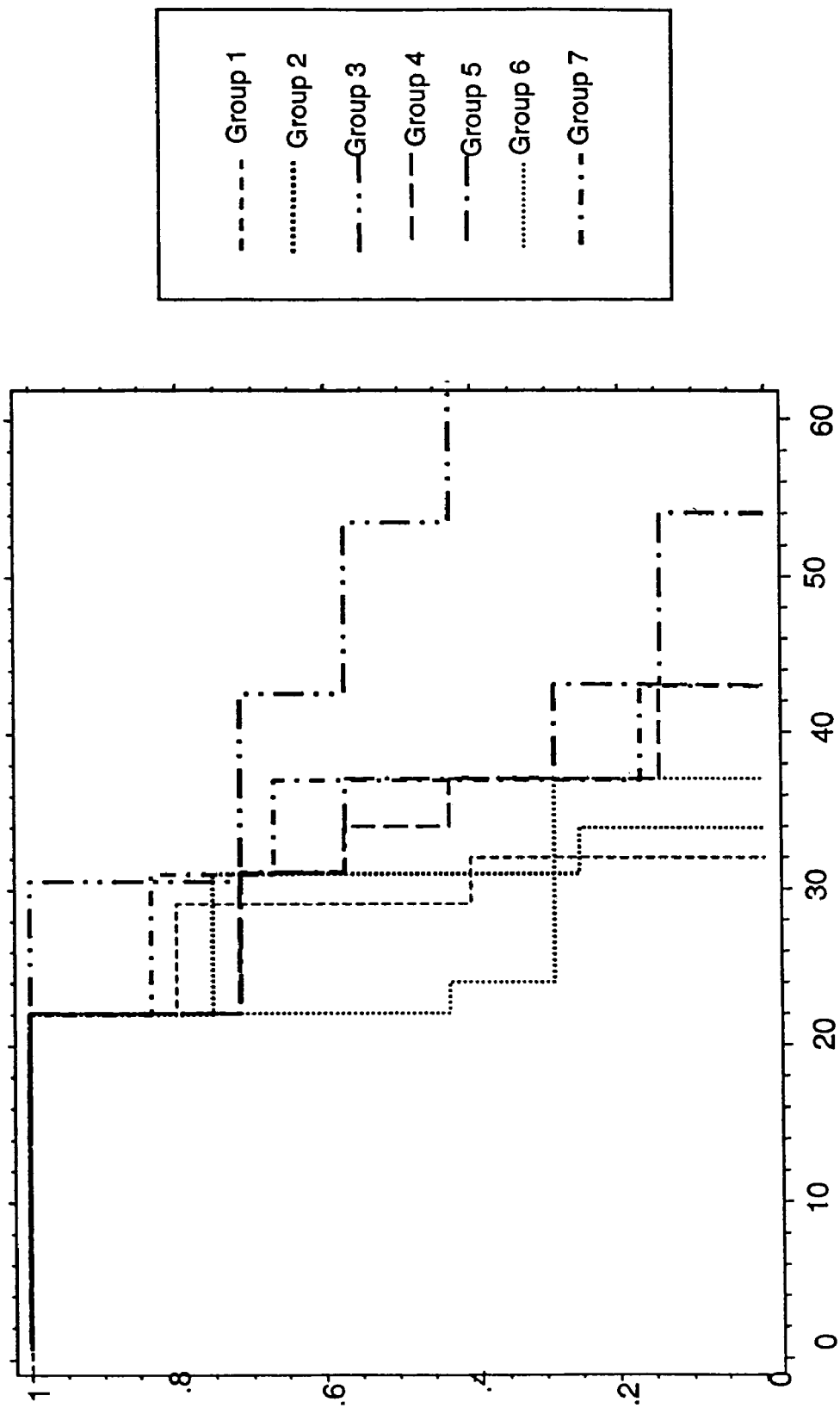
FIG. 2 is a graphical representation of the results of the murine xenograft prostate cancer model described in Example 2 herein. The vertical axis represents cumulative survival as a fraction of the starting number of animals remaining alive. The horizontal graph represents time in Days.

Days of survival after injection were plotted using a Kaplan Meier survival and the results of treatment groups 1–4 are presented graphically in FIG. 2 of the attached drawings. Comparison among groups was performed using the Logrank Test (Statview Software) Differences were considered significant if $p<0.05$.

As can be seen from the data presented, treatment with ACN53 formulations containing icodextrin resulted in a statistically significant prolongation of survival as compared to ACN53 formulated in vPBS or controls at a viral dose of $5 \times 10^{10}$ viral particles. One animal receiving the maximal viral dose in icodextrin was free of clinical signs of tumor growth upon completion of the study (Day 100). This animal had minimal tumor growth in the peritoneal cavity indicated that the animal was injected with tumor cells and that tumor formed but that tumor growth was inhibited.

Example 3

Efficacy of Icodextrin rAd-p53 Formulation in Murine Xenograft Ovarian Cancer Model The effect of icodextrin containing adenoviral formulations containing (Formulations B and C in Table 2 above) was evaluated in a murine intraperitoneal xenograft model of human ovarian cancer. The experiment was conducted in substantial accordance with the teaching of Example 2 above with the following variations. Animals were inoculated intraperitoneally with $1 \times 10^7$ human MDL-H2774 ovarian cancer cells (ATCC CRL-10303) cells in 0.2 ml of HBSS. The animals were dosed intraperitoneally with 0.5 ml formulations B and C above on Days 2, 5, 8 and 12. Control groups were treated as in Example 2. Similar prolongation of survival was observed in this model system with adenovirus formulations comprising icodextrin.

Examnle 4 vIco Enhanced Efficacy of an Oncolytic Adenovirus in an Orthotopic Model of Human Ovarian Cancer A murine model of human ovarian cancer was employed to evaluate the effect of icodextrin containing formulations of a conditionally replicating adenoviral vector. The model was established in nude mice (20–25 g commercially available from Harlan, Indianapolis, Ind.) by the administration of a single intraperitoneal injection of a suspension of $1 \times 10^7$ MDA H2774 human ovarian cancer cells (available from the American Type Culture Collection under Accession Number CRL-10303) in 0.5 ml in Hank's Balanced Salt Solution (HBSS). Tumors were permitted to grow for 7 days and the mice were evaluated for the presence of palpable tumors. Those mice evidencing tumors were separated into groups for treatment.

A conditionally replicating recombinant adenoviral vector designated K9TB was prepared in substantial accordance with the teaching of Ramachandra, et al. (PCT International Publication Number WO 00/22137 published Apr. 20, 2000). The K9TB virus is a conditionally replicating virus containing a deletion of a amino acids 4–25 of the E1a region, a p53 response element driving expression of the E2F-Rb fusion protein (Antelman, et al., U.S. Pat. No. 6,074,850 issued Jun. 13, 2000) inserted into the E3 region.

The following formulations provided in Table 5 below were prepared for evaluation in the tumor model described above.

TABLE 5

| | | Formulations | | |
|---|---|---|---|---|
| Name | Description | vPBS (1) (microliters) | vICO (2) (milliliters) | virus (3) (microliters) |
| H | 15% vICO control | — | 3 | — |
| I | vPBS control | 3 | — | — |
| J | $4.5 \times 10^8$ PN K9TB; vPBS | 3.757 | — | 743 |
| K | $4.5 \times 10^8$ PN K9TB; 15% vICO | — | 3.757 | 743 |

Notes:
(1) "vPBS" solution is a sterile solution 3% sucrose, 2 mM MgCl$_2$ in phosphate buffered saline, pH7.4.
(2) "vICO" is a sterile 15% icodextrin solution 95 millimolar Na$^+$, 1.75 millimolar Ca$^{++}$, 2.0 millimolar Mg$^{++}$, 59 millimolar Cl$^-$, 40 millimolar lactate, 88 millimolar sucrose, 160 gl/liter icodextrin.
(3) "virus" refers to a 1:1000 dilution of a stock virus suspension containing $6.06 \times 10^{11}$ K9TB viral particles per milliliter.

The tumor bearing animals were segregated into the following groups for treatment:

TABLE 6

| | Treatment Groups | | |
|---|---|---|---|
| Group | n | Formulation | Total K9TB Dose (particles) |
| 1 | 4 | H | — |
| 2 | 4 | I | — |
| 3 | 7 | J | $2 \times 10^8$ |
| 4 | 7 | K | $2 \times 10^8$ |

Each group was provided a treatment regimen consisting of a single intraperitoneal injection of 0.5 ml the appropriate formulation on Days days 7, 9, 12, and 14 following injection of tumor cells. Upon completion of the treatment regimen, the animals were randomly caged and monitored daily (blinded) for moribund animals as characterized by visible loss of body weight hunched back, and sedation. Moribund animals were sacrificed and examined gross pathologically. Animal number, date of sacrifice (or found dead) and gross pathological findings the results summarized in Table 7 below.

TABLE 7

| | Results of H2774 Ovarian Tumor Model | | | |
|---|---|---|---|---|
| | | Survival Time (Days) | | |
| Group | Formulation | mean | minimum | maximum |
| 1 | H | 28.5 | 28 | 29 |
| 2 | I | 28.3 | 28 | 29 |
| 3 | J | 41.0 | 36 | 47 |
| 4 | K | 55.7 | 41 | 80* |

*the experiment was concluded on Day 80

Figure 3:
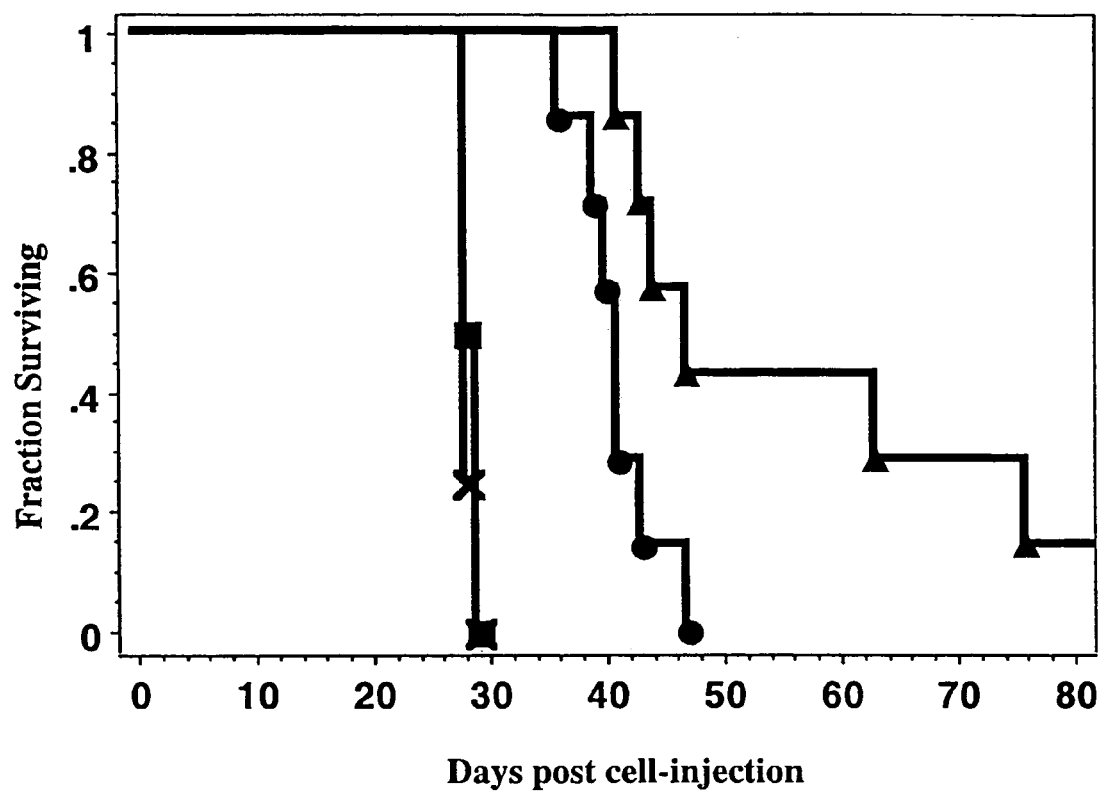
FIG. 3 is a graphical representation of the data generated from the murine model of ovarian cancer more fully described in Example 4 herein. drawings. Formulation H/Treatment Group 2 is represented by X, Formulation I/Treatment Group 1 is represented by squares, Formulation J/Treatment Group 3 is represented by circles; and Formulation L/Treatment Group 4 is represented by triangles.

Days of survival after injection were summarized using a Kaplan-Meier plot and the results of treatment groupd 1–4 are presented graphically in FIG. 3 of the attached drawings. Comparison among groups was performed using the Logrank Test (Statview Software). Differences were considered significant if p<0.05.

A graphical representation of the data is presented in FIG. 3 of the attached drawings. Formulation H/Treatment Group 2 is represented by X, Formulation I/Treatment Group 1 is represented by squares, Formulation J/Treatment Group 3 is represented by circles; and Formulation L/Treatment Group 4 is represented by triangles. As can be seen from the data presented, the treatment of tumor bearing mice with the recombinant adenoviral vector K9TB in both the vico and vPBS formulations prolonged survival compared to the vehicle controls. However, K9TB formulated in vlco demonstrated a prolongation of survival compared to K9TB formulated in vPBS (p<0.01, n=7 animals/treatment group).

The invention claimed is:

1. A method to deliver a recombinant nucleic acid to a cell, the method comprising intraperitoneally contacting the cell with a solution comprising:
   an adenoviral vector, the adenoviral vector comprising the recombinant nucleic acid,
   about 2%–20% w/v dextrin, and
   about 1%–10% w/v sucrose.

2. The method according to claim 1 wherein the molecular weight of the dextrin is in the range from about 1,000–200,000.

3. The method according to claim 2 wherein the molecular weight of the dextrin is between about 2,000–55,000.

4. The method according to claim 3 wherein the dextrin contains more than about 15% w/v of polymers of a degree of polymerisation greater than 12.

5. The method according to claim 4 wherein the dextrin contains more than about 50% w/v of polymers of a degree of polymerisation greater than 12.

6. The method according to claim 5 wherein the dextrin is present in the solution in an amount of less than about 20% w/v.

7. The method according to claim 6 wherein the dextrin is present in the solution in an amount selected from about: 2% w/v; 3% w/v; 4% w/v; 5% w/v; 6% w/v; 7% w/v; 8% w/v; 9% w/v; 10% w/v; 11% w/v; 12% w/v; 13% w/v; 14% w/v; 15% w/v; 16% w/v; 17% w/v; 18% w/v; 19% w/v; 20% w/v.

8. The method according to claim 1 wherein the dextrin is about 4% w/v.

9. The method according to claim 1 wherein the sucrose is an amount of between about 2 and 5% w/v.

10. The method according to claim 9 wherein the amount of sucrose is about 3% w/v.

11. The method according to claim 1 wherein the amount of dextrin is about 15% w/v and the amount of sucrose is about 3% w/v.

12. The method according to claim 11 wherein the amount of dextrin is about 4% w/v and the amount of sucrose is about 3% w/v.

13. The method according to claim 1 wherein the solution further comprises a divalent cation.

14. The method according to claim 13 wherein the divalent cation is in a concentration of at least 0.2 mM.

15. The method according to claim 14 wherein the divalent cation concentration is between 0.2–3.0 mM.

16. The method according to claim 15 wherein the divalent cation is provided by $MgCl_2$ and the concentration is about 2.0 mM.

17. The method according to claim 16 wherein the solution comprises about 4% w/v dextrin, about 3% w/v sucrose and about 2.0 mM $MgCl_2$.

18. The method of claim 1 wherein said adenovirus further encodes an exogenous transgene.

19. The method of claim 18 wherein said transgene is a tumor suppressor gene.

20. The method of claim 19 wherein said tumor suppressor gene is p53.

21. The method of claim 1 wherein said adenoviralvector is replication competent.

22. The method of claim 21 wherein said vector is a conditionally replicating replication competent vector.

23. A composition for intraperitoneal delivery of a recombinant adenoviral vector to a cell, the composition comprising a recombinant adenoviral vector in a solution comprising about 2%–20% w/v dextrin and about 1%–10% sucrose.

24. The composition of claim 23 wherein the adenoviral vector is a replication competent adenoviral vector.

25. A pharmaceutical formulation comprising a recombinant adenoviral vector, about 2%–20% w/v dextrin, about 1%–10% sucrose and a divalent cation.

26. The composition of claim 23 wherein the adenoviral vector is a conditionally-replicating replication competent adenoviral vector.

* * * * *

UNITED STATES PATENT AND TRADEMARK OFFICE
CERTIFICATE OF CORRECTION

PATENT NO. : 7,094,583 B2
APPLICATION NO. : 10/913567
DATED : August 22, 2006
INVENTOR(S) : Susan E. Conroy et al.

Page 1 of 1

It is certified that error appears in the above-identified patent and that said Letters Patent is hereby corrected as shown below:

On the title page, in column 1, at (75) the inventor name "Engler Heidrun" should read --Heidrun Engler--.

Signed and Sealed this

Ninth Day of January, 2007

JON W. DUDAS
*Director of the United States Patent and Trademark Office*